(12) United States Patent
Engelbart et al.

(10) Patent No.: US 7,576,850 B2
(45) Date of Patent: Aug. 18, 2009

(54) IN-PROCESS VISION DETECTION OF FLAWS AND FOD BY BACK FIELD ILLUMINATION

(75) Inventors: Roger W. Engelbart, St. Louis, MO (US); Reed Hannebaum, Mount Vernon, IL (US); Tim Pollock, Ballwin, MO (US)

(73) Assignee: The Boeing Company, Chicago, IL (US)

( * ) Notice: Subject to any disclaimer, the term of this patent is extended or adjusted under 35 U.S.C. 154(b) by 0 days.

(21) Appl. No.: 12/179,674

(22) Filed: Jul. 25, 2008

(65) Prior Publication Data

US 2008/0278716 A1    Nov. 13, 2008

Related U.S. Application Data

(62) Division of application No. 10/904,719, filed on Nov. 24, 2004.

(51) Int. Cl.
*G01N 21/00* (2006.01)

(52) U.S. Cl. .................................. 356/237.2; 356/237.3

(58) Field of Classification Search ... 356/237.1–237.6, 356/238.1–239.7, 429–430; 250/306–308, 250/559.15, 559.04–559.06; 348/86–92, 348/125–134; 700/108–110; 438/16; 156/64, 156/378–379; 382/141, 143–153, 112
See application file for complete search history.

(56) References Cited

U.S. PATENT DOCUMENTS

| | | | |
|---|---|---|---|
| 3,243,509 A | 3/1966 | Stut | |
| 3,879,245 A | 4/1975 | Fetherson et al. | |
| 4,064,534 A | 12/1977 | Chen et al. | |
| 4,120,402 A | 10/1978 | Swanson | |
| 4,135,204 A | 1/1979 | Davis et al. | |
| 4,310,132 A | 1/1982 | Frosch et al. | |
| 4,437,115 A | 3/1984 | Yoshida | |
| 4,445,185 A | 4/1984 | Davis, Jr. et al. | |

(Continued)

FOREIGN PATENT DOCUMENTS

EP        0319797 A2    6/1989

(Continued)

OTHER PUBLICATIONS

R. Paulson et al., Infrared Imaging Techniques for Flaw Detection in Composite Materials, Lockheed Missiles and Space Company, Inc., Sunnyvale, CA, pp. 88-95.

(Continued)

*Primary Examiner*—Michael A Lyons
*Assistant Examiner*—Tri T Ton
(74) *Attorney, Agent, or Firm*—Ostrager Chong Flaherty & Broitman P.C.

(57) ABSTRACT

A flaw and foreign object debris (FOD) detection system (11) for use during fabrication of a structure (12) includes an illumination device (13). The illumination device (13) is configured to be in proximity with a fabrication system (10) and illuminates a portion (18) of the structure (12). The illumination device (13) directs light rays (16) at acute angles relative to the portion (18). A detector (14) monitors the portion (18) and detects FOD in the portion (18) during fabrication of the structure (12) in response to the reflection of the light rays (16) off of the portion (18).

16 Claims, 6 Drawing Sheets

U.S. PATENT DOCUMENTS

| | | |
|---|---|---|
| 4,548,859 A | 10/1985 | Kline et al. |
| 4,608,220 A | 8/1986 | Caldwell et al. |
| 4,672,678 A | 6/1987 | Koezuka et al. |
| 4,693,678 A | 9/1987 | Von Volkli |
| 4,699,683 A | 10/1987 | McCowin |
| 4,706,296 A | 11/1987 | Pedotti et al. |
| 4,760,444 A | 7/1988 | Nielson et al. |
| 4,780,262 A | 10/1988 | Von Volkli |
| 4,790,023 A | 12/1988 | Matsui et al. |
| 4,790,898 A | 12/1988 | Woods |
| 4,830,298 A | 5/1989 | Van Blunk |
| 4,877,471 A | 10/1989 | McCowin et al. |
| 4,941,182 A | 7/1990 | Patel |
| 4,975,863 A | 12/1990 | Sistler et al. |
| 5,007,096 A | 4/1991 | Yoshida |
| 5,012,523 A | 4/1991 | Kobayashi et al. |
| 5,016,099 A | 5/1991 | Bongardt et al. |
| 5,024,399 A | 6/1991 | Barquet et al. |
| 5,032,211 A | 7/1991 | Shinno et al. |
| 5,058,174 A | 10/1991 | Carroll |
| 5,058,497 A | 10/1991 | Bishop et al. |
| 5,187,573 A | 2/1993 | Yoshida |
| 5,198,983 A | 3/1993 | Blake et al. |
| 5,231,675 A | 7/1993 | Sarr et al. |
| 5,237,407 A | 8/1993 | Crezee et al. |
| 5,253,302 A | 10/1993 | Massen |
| 5,258,917 A | 11/1993 | Bruder et al. |
| 5,263,094 A | 11/1993 | Laitinen et al. |
| 5,331,312 A | 7/1994 | Kudoh |
| 5,333,208 A | 7/1994 | Massen |
| 5,337,647 A | 8/1994 | Roberts et al. |
| 5,426,509 A | 6/1995 | Peplinski |
| 5,439,549 A | 8/1995 | Fryc et al. |
| 5,440,650 A | 8/1995 | Hieda et al. |
| 5,450,147 A | 9/1995 | Dorsey-Palmateer |
| 5,452,370 A | 9/1995 | Nagata |
| 5,486,819 A | 1/1996 | Horie |
| 5,518,208 A | 5/1996 | Roseburg |
| 5,533,628 A | 7/1996 | Tao |
| 5,540,126 A | 7/1996 | Piramoon |
| 5,562,788 A | 10/1996 | Kitson et al. |
| 5,626,471 A | 5/1997 | Howie et al. |
| 5,646,682 A | 7/1997 | Sogabe et al. |
| 5,651,600 A | 7/1997 | Dorsey Palmateer |
| 5,652,432 A | 7/1997 | Yaginuma |
| 5,683,646 A | 11/1997 | Reiling et al. |
| 5,700,337 A | 12/1997 | Jacobs et al. |
| 5,703,784 A | 12/1997 | Pearson |
| 5,732,147 A | 3/1998 | Tao |
| 5,742,504 A | 4/1998 | Meyer et al. |
| 5,746,553 A | 5/1998 | Engwall |
| 5,804,276 A | 9/1998 | Jacobs et al. |
| 5,814,386 A | 9/1998 | Vasiliev et al. |
| 5,825,495 A | 10/1998 | Huber |
| 5,862,372 A | 1/1999 | Morris et al. |
| 5,871,117 A | 2/1999 | Protasov et al. |
| 5,917,588 A | 6/1999 | Addiego |
| 5,963,660 A | 10/1999 | Koontz et al. |
| 5,979,531 A | 11/1999 | Barr et al. |
| 6,012,883 A | 1/2000 | Engwall et al. |
| 6,013,341 A | 1/2000 | Medvedev et al. |
| 6,026,883 A | 2/2000 | Hegerhorst et al. |
| 6,045,651 A | 4/2000 | Kline et al. |
| 6,064,429 A | 5/2000 | Belk et al. |
| 6,074,716 A | 6/2000 | Tsotsis |
| 6,086,696 A | 7/2000 | Gallaher |
| 6,087,654 A | 7/2000 | Durham et al. |
| 6,112,792 A | 9/2000 | Barr et al. |
| 6,122,065 A | 9/2000 | Gauthier |
| 6,168,358 B1 | 1/2001 | Engwall et al. |
| 6,205,239 B1 | 3/2001 | Lin et al. |
| 6,229,972 B1 | 5/2001 | Rushing |
| 6,364,250 B1 | 4/2002 | Brinck et al. |
| 6,369,492 B1 | 4/2002 | Sugimoto |
| 6,381,366 B1 | 4/2002 | Taycher et al. |
| 6,390,169 B1 | 5/2002 | Johnson |
| 6,408,429 B1 | 6/2002 | Marrion, Jr. et al. |
| 6,451,152 B1 | 9/2002 | Holmes |
| 6,480,271 B1 | 11/2002 | Cloud et al. |
| 6,542,235 B1 | 4/2003 | Caskey et al. |
| 6,547,769 B2 | 4/2003 | Van Tassel et al. |
| 6,639,662 B2 | 10/2003 | Vaez-Iravani et al. |
| 6,648,273 B2 | 11/2003 | Anast |
| 6,692,681 B1 | 2/2004 | Lunde |
| 6,723,951 B1 | 4/2004 | McGraw |
| 6,725,123 B1 | 4/2004 | Denuell |
| 6,744,913 B1 | 6/2004 | Guest et al. |
| 6,799,619 B2 | 10/2004 | Holmes et al. |
| 6,814,822 B2 | 11/2004 | Holmes |
| 6,871,684 B2 | 3/2005 | Engelbart et al. |
| 7,039,485 B2 | 5/2006 | Engelbart |
| 7,048,024 B2 | 5/2006 | Clark |
| 7,080,441 B2 | 7/2006 | Braun |
| 7,083,698 B2 | 8/2006 | Engwall |
| 7,134,629 B2 | 11/2006 | Johnson |
| 7,137,182 B2 | 11/2006 | Nelson |
| 7,159,822 B2 | 1/2007 | Grantham et al. |
| 7,171,033 B2 | 1/2007 | Engelbart |
| 7,193,696 B2 | 3/2007 | Engelbart |
| 7,228,611 B2 | 6/2007 | Anderson |
| 7,236,625 B2 * | 6/2007 | Engelbart et al. ........... 382/141 |
| 7,263,625 B2 | 8/2007 | Katoh et al. |
| 7,282,107 B2 | 10/2007 | Johnson |
| 7,289,656 B2 | 10/2007 | Engelbart |
| 7,325,771 B2 | 2/2008 | Stulc |
| 2003/0102070 A1 | 6/2003 | Black et al. |
| 2006/0073309 A1 | 4/2006 | Hogg |

FOREIGN PATENT DOCUMENTS

| | | |
|---|---|---|
| EP | 0833146 A2 | 1/1998 |
| EP | 0903574 A2 | 1/1998 |
| EP | 1030172 | 8/2000 |
| EP | 1334819 | 8/2003 |
| EP | 1503206 | 2/2005 |
| JP | 2001012930 | 1/2001 |
| WO | 94/18643 | 8/1994 |
| WO | 2004/025385 | 3/2004 |

OTHER PUBLICATIONS

Lichtenwalner, P.F., Neural Network-Based Control for the Fiber Placement Composite Manufacturing Process, Journal of Materials Engineering and Performance, vol. 2(5), Oct. 1993, p. 687.

Wang, Eric L., Effects of Laps and Gaps on the Processing of Advanced Thermoplastic Composites, Thesis, Massachusetts Institute of Technology, Jan. 1991.

Krupka, R; Walz, T; Ettemeyer, A: "Industrial Applications of Shearography for Inspection of Aircraft Components" Proceedings of the 8th European Conference of Nondestructicve Testing< Barcelona (Spain), Jun. 17-21, 2002, 'Online! Jun. 30, 2002, XP002351899 NDT.NET—Feb. 2003, vol. 8, No. 2 Retrieved from the Internet: URL:http://www.ndt.net/articl/encndt02/484/484.htm> 'retrieved on Oct. 31, 2005.

The Written Opinion for International Application PCT/US2004/039905, dated May 25, 2005 6 pages.

International Search Report dated May 25, 2005 for report for International Application PCT/US2004/039905, dated Nov. 30, 2004, 4 pages.

Prof. J. Zhang: "Angewandte Sensorik" Ch. 4, Sensoren in Der Robotik, Nov. 11, 2003; (retrieved from the Internet, URL:http://tech-www.Informatik.uni-hamburgnsorik/vorlesung_03.pdf) retrieved on Apr. 2004! p. 89, 20 pages.

European Search Report, Application No. 04076900.2, dated Dec. 1, 2004, 4 pages.

Fiedler, L., et al, "Tango Composite Fuselage Platform", SAMPE Journal, vol. 39, No. 1, Jan./Feb. 2003, pp. 57-63.

Advanced Technology Tape Laying for Affordable Manufacturing of Large Composite Structures; http://www.cinmach.com/tech/pdf/TapeLayingGrimshaw.pdf; Michael N. Grimshaw, et al; 11 pages.

Fiber Placement; http://www.cinmach.com/tech/pdf/asm_chapter_fp.pdf; Don O. Evans; Cincinnati Machine; 3 pages.

Automated Tape Laying; http://www.cinmach.com/tech/pdf/Grimshaw%20ASM%20Handbook.pdf; Michael N. Grimshaw; Cincinnati Machine; 6 pages.

Raytheon Aircraft's Hawker Horizon Reaches Fuselage Milestone, Raytheon News Release; http://www.beechcraft.de/Presse/2000/100900b.htm; 2 pages.

BAe 146, Flight International, May 2, 1981, 2 pages.

A Barrelful of Experience, Intervia, May 1992, 2 pages.

Raytheon, Mar. 2000, vol. 4, No. 2, http://www.cs.com/king/vasci/newsletter/vol42.html, 2 pages.

Business Aviation, Jun. 7, 2002, http://www.aviationnow.com/avnow/news/channel_busav.jsp?view=story&id=news/btoyo0607.xml, 1 page.

Beechcraft's Composite Challenge, http://www.aerotalk.com/Beech.cfm, 2 pages.

Sharp et al., "Material Selection/Fabrication Issues for Thermoplastic Fiber Placement", Journal of Thermoplastic Composite Materials, vol. 8; Jan. 1995, p. 2-14.

http://www.cinmach.com/WolfTracks4-1/MTG-WT7.htm; Premier I Features Lighter, Stronger, All-Conmposite Fuselage, 1 page.

http://www.cinmach.com/compnews/PressReleases/pr00-11.htm; Raytheon Aircraft Orders Four More Fiber Cincinnati Fiber Placement Systems for Industry's First Composite-Fuselage Busines Jets, 1 page.

http://www.rockymountaincomposites.com/wind-sys.htm: Filament Winding, 2 pages.

PCT Intl Written Opinion for Application No. PCT/US2006/031305, dated Feb. 11, 2008, 5 pages.

Assembly Guidance Systems website at http://www.assemblyguide.com/HAMPI/Hampi.htm, "automatic Ply Verification", 2 pages, printed Oct. 17, 2005.

UltraOptec, Inc. website at http://www.ultraoptec.com/luis-747.html, "Luis 747", 17 pages, printed Oct. 17, 2005.

Engelbart, Roger W., et al., In-Process Monitoring of Pre-Staged Fiber Placement Tows Using Nuclear Magnetic Resonance (NMR), Proceedings of the 43rd International SAMPE Symposium, Anaheim, California, May 31-Jun. 4, 1998.

Thomas, Matthew M. et al., Manufacturing of Smart Structures Using Fiber Placement Manufacturing Processes; SPIE, vol. 2447, pp. 266-273 (1995).

Elliott, Augustus W., Fiber Placement Inspection System and Experimental Approach; 43d Int'l SAMPE Symposium, pp. 957-963 (Society for the Advancement of Material and Process Engineering) (1998).

* cited by examiner

IN-PROCESS VISION DETECTION OF FLAWS AND FOD BY BACK FIELD ILLUMINATION

CROSS REFERENCE TO RELATED APPLICATIONS

The present invention is a divisional application of U.S. patent application Ser. No. 10/904,719 (filed on Nov. 24, 2004 by Engelbart et al., published on May 25, 2006 under U.S. Pat. Appl. Publ. No. 2006/0108048), which is related to U.S. patent application Ser. Nos. 10/846,974 (filed on May 14, 2004 by Engelbart et al., published on Feb. 3, 2005 under U.S. Pat. Appl. Publ. No. 2005/0025350), U.S. Ser. No. 10/217,805 (filed on Aug. 13, 2002 by Engelbart et al. and published on Feb. 19, 2004 under U.S. Pat. Publ. No. 2004/0031567), U.S. Ser. No. 09/819,922 (filed Mar. 28, 2001 and published on Oct. 3, 2002 under U.S. Pat. Appl. Publ. No. 2002/0141632), U.S. Ser. Nos. 11/202,411, 11/264,076 and U.S. Pat. No. 6,871,684.

TECHNICAL FIELD

The present invention relates generally to the fabrication of composite structures. More particularly, the present invention relates to systems and methods of detecting flaws and foreign object debris (FOD) during the fabrication of a composite structure.

BACKGROUND OF THE INVENTION

Composite structures have been known in the art for many years. Although composite structures can be formed in many different manners, one advantageous technique for forming composite structures is a fiber placement or automated collation process. According to conventional automated collation techniques, one or more ribbons of composite material, known as composite strands or tows, are laid down on a substrate. The substrate may be a tool or mandrel, but more conventionally, is formed of one or more underlying layers of composite material that have been previously laid down and compacted.

Conventional fiber placement processes in the formation of a part utilize a heat source to assist in the compaction of the plies of composite material at a localized nip point. In particular, the ribbons or tows of the composite material and the underlying substrate are heated at the nip point to increase resin tack while being subjected to compressive forces to ensure adhesion to the substrate. To complete the part, additional strips of composite material can be applied in a side-by-side manner to each layer and can be subjected to localized heat and pressure during the consolidation process.

Unfortunately, defects can occur during the placement of the composite strips onto the underlying composite structure. Such defects can include tow gaps, overlaps, dropped tows, puckers, and twists. Additionally, foreign objects and debris (FOD), such as resin balls and fuzz balls, can accumulate on a surface of the composite structure. Resin balls are small pieces of neat resin that build up on the surfaces of the fiber placement head as the preimpregnated tows pass through the guides and cutters. The resin balls become dislodged due to the motion and vibration of the fiber placement machine, and drop on to the surface of the ply. Subsequent courses of applied layers cover the resin ball and a resultant bump is created in the laminate whereat there may be no compaction of the tows. The fuzz balls are formed when fibers at the edges of the tows fray and break off as the tows are passed through the cutter assembly. The broken fibers collect in small clumps that fall onto the laminate and are covered by a subsequent layer.

Composite laminates fabricated by fiber placement processes are typically subjected to a 100 percent ply-by-ply visual inspection for both defects and FOD. Typically, these inspections are performed manually during which time the fiber placement machine is stopped and the process of laying materials halted until the inspection and subsequent repairs, if any, are completed. In the meantime, the fabrication process has been disadvantageously slowed by the manual inspection process and machine downtime associated therewith.

Current inspection systems are capable of identifying defects in a composite structure during the fabrication process without requiring machine stoppage for manual inspections. The inspection systems are capable of detecting and identifying FOD "in-process" or during the fabrication of a composite structure. This, in turn, eliminates the need for manual FOD inspections and the machine downtime associated therewith.

A split illumination technique has been introduced for the detection of flaws and FOD simultaneously. A first half of a viewing area, referred to as the bright field, is illuminated. A second half of the viewing area, referred to as the dark field, is not illuminated. The flaws in the composite structure are detectable within the bright field, but are indistinguishable in the dark field. The FOD is detectable in the dark field, but is indistinguishable in the bright field. Thus, the split illumination technique requires the use of dual illumination levels. The use of dual illumination levels complicates the inspection process by causing a single field to be viewed twice, which is time consuming. A single field must be viewed twice to inspect for both flaws and FOD.

Thus, there exists a need for an improved system and method of the detection and identification of flaws and FOD within a composite structure during the fabrication thereof that simplifies and minimizes the time involved in the inspection of that composite structure.

SUMMARY OF THE INVENTION

The present invention provides a flaw and foreign object debris (FOD) detection system for use during the fabrication of a structure. The detection system includes an illumination device. In one embodiment of the present invention, the illumination device is configured to be in proximity with a fabrication system and illuminates a portion of the structure. The illumination device directs light rays at acute angles relative to the portion. A detector monitors the portion and detects FOD in the portion during fabrication of the structure in response to reflection of the light rays off of that portion.

In another embodiment of the present invention, the illumination device directs light rays, having a single illumination level, at the portion and at acute angles relative to the portion. A detector monitors the portion and detects a flaw and FOD simultaneously in the portion during fabrication of the structure.

The embodiments of the present invention provide several advantages. One such advantage is the provision of a composite structure in-process fabrication inspection technique that allows for the simultaneous detection of flaws and FOD for a single field of inspection.

Another advantage provided by an embodiment of the present invention, is the provision of a composite structure in-process fabrication inspection technique that allows for the simultaneous detection of flaws and FOD using a single illumination level.

Furthermore, the present invention simplifies the composite structure inspection process and minimizes the time involved therein.

Moreover, the present invention allows for the in-process repair of a composite structure upon detection of a flaw or FOD.

The present invention itself, together with further objects and attendant advantages, will be best understood by reference to the following detailed description, taken in conjunction with the accompanying drawing.

DETAILED DESCRIPTION

Figure 1:
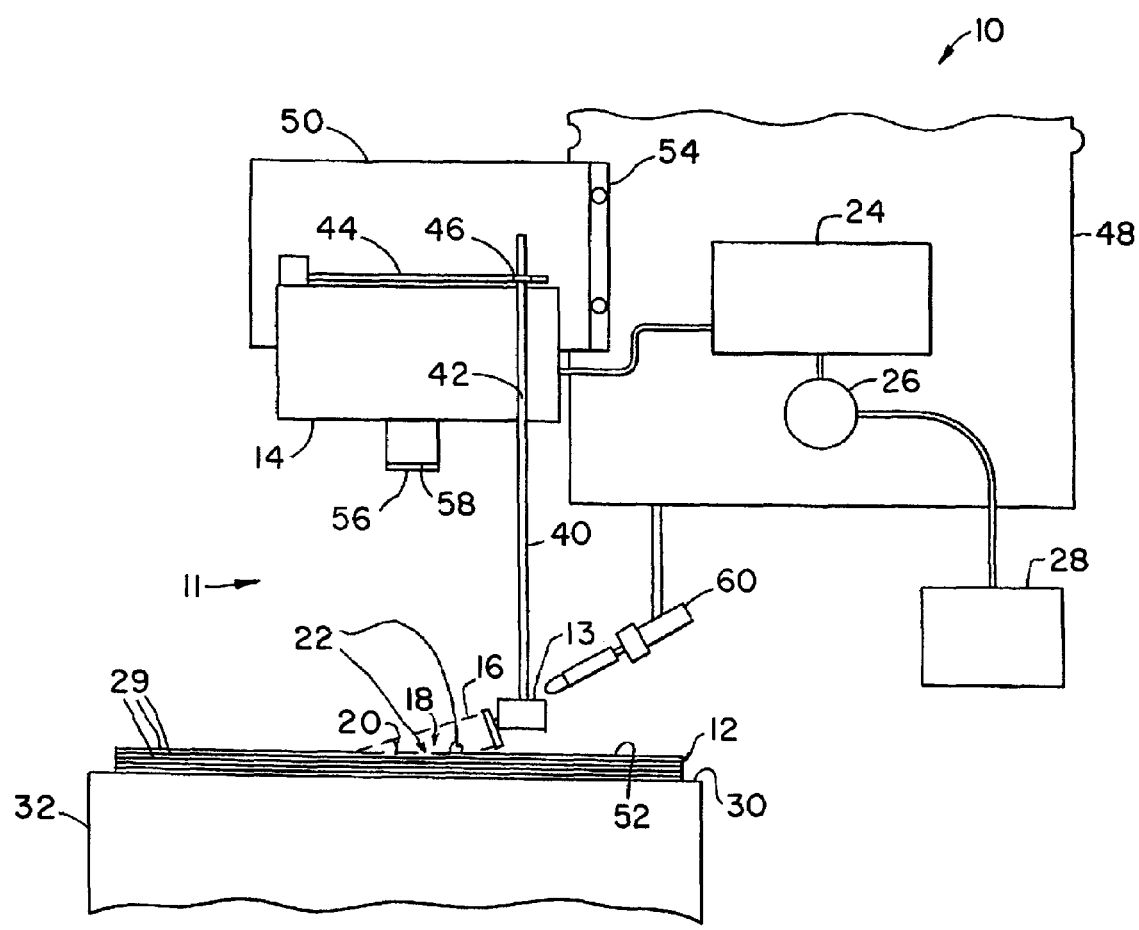
FIG. 1 is a side schematic view of a fabrication system incorporating a flaw and FOD detection system in accordance with an embodiment of the present invention.

In each of the following Figures, the same reference numerals are used to refer to the same components. While the present invention is described with respect to systems and methods of detecting flaws and foreign object debris (FOD) during the fabrication of a composite structure, the present invention may be adapted for various applications and systems, such as fabrication of structures and components, production line applications, or other applications and systems known in the art. The present invention may be applied to both the fabrication of aeronautical and non-aeronautical systems and components.

In the following description, various operating parameters and components are described for one constructed embodiment. These specific parameters and components are included as examples and are not meant to be limiting.

Also, in the following description the term "foreign object debris (FOD)" refers to any resin ball, fuzz ball, impurity, or other foreign or undesirable object contained within or on a composite structure. FOD may refer to one or more of the stated objects.

In addition, the term "flaw" refers to any defect within a composite structure or structure under fabrication. A flaw may refer to a tow gap, an overlap of material, a dropped tow, a pucker, a twist or any other flaw known in the art.

Figure 2:
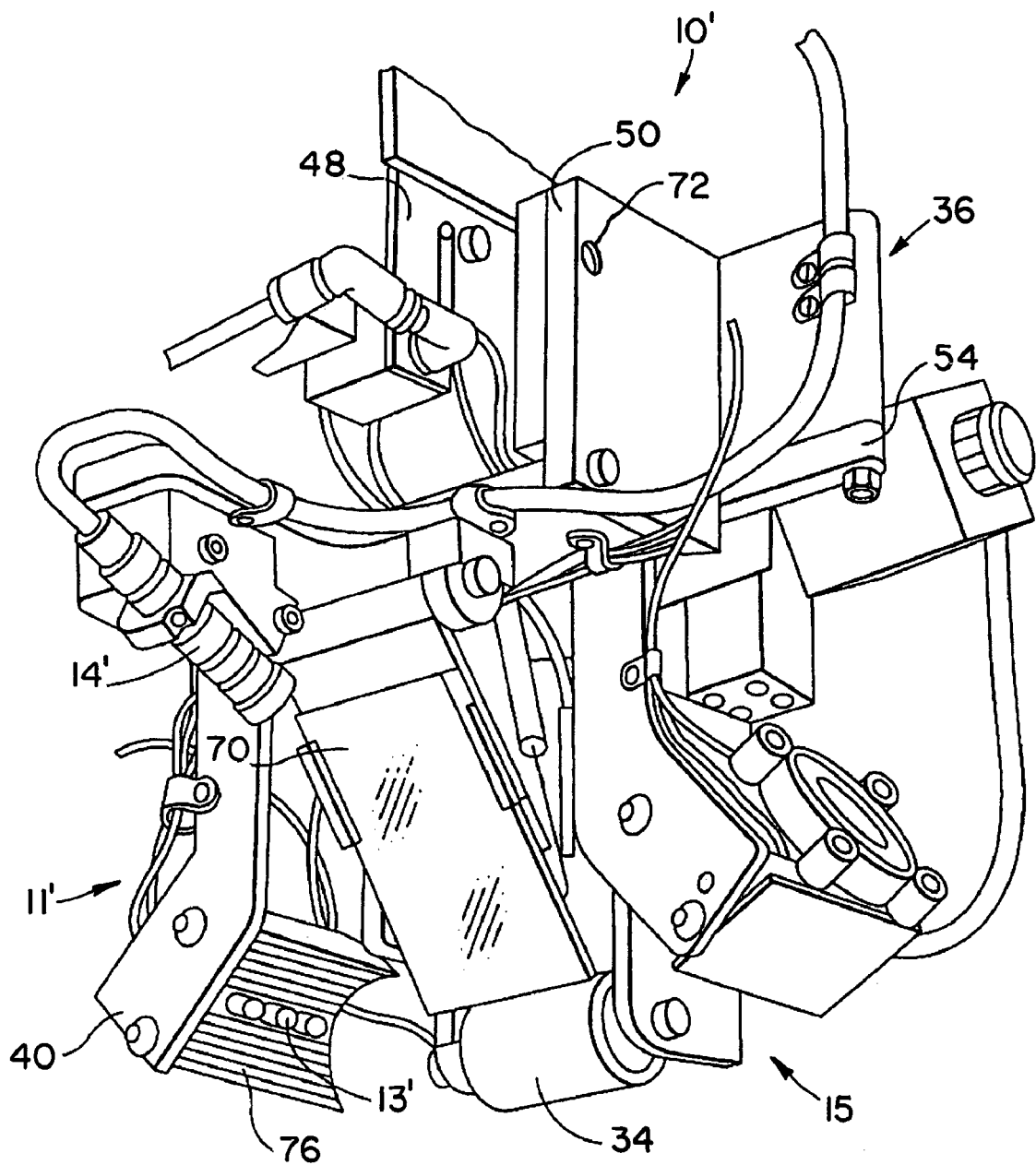
FIG. 2 is a perspective view of an application portion of a fabrication system incorporating a flaw and FOD detection system in accordance with another embodiment of the present invention.

Referring now to FIG. 1, a side schematic view of a fabrication system 10 is shown incorporating a flaw and FOD detection and inspection system 11 in accordance with an embodiment of the present invention. The fabrication system 10 includes a lamination system 15, as best seen in FIG. 2, that may utilize an automated collation process to form a composite structure 12, as shown. The detection system 11 is positioned proximate the composite structure 12 and includes one or more illumination devices or light sources 13 (only one is shown) and one or more detectors 14 (only one is shown). The light sources 13 generate light arrays 16 that are directed at a portion 18 of the composite structure 12 at low incident angles 20 and at a single illumination level to reveal flaws and FOD 22 simultaneously within that portion 18. A controller 24 is coupled to the detectors 14 and interprets data received therefrom, which may be in the form of images. The data may be used to adjust the operation of the fabrication system 10, the detection system 11, and the lamination system 15, and to indicate, detect, and allow for the correction of the flaws and FOD 22. The controller 24 may store the received data and/or related information in the memory or storage device 26. System parameters and operation may be adjusted via the user interface 28.

During the fabrication of the composite structure 12, the composite structure 12 may be formed of adjacent tows or strips of composite tape (not shown) to form layers 29. The strips include multiple fibers that are embedded in a resin or other material, which becomes tacky or flowable upon the application of heat. The lamination system 15 arranges the strips on a work surface 30 of a table, mandrel, or tool 32, and compacted with a compaction roller to form the composite structure 12. A compaction roller 34 can be seen in FIG. 2. The automated collation process includes guiding the composite strips from material creels (not shown) to an automated collation or fiber placement machine, such as a machine made by Cincinnati Milacron and Ingersoll Milling Machines. In particular, the composite strips are guided to a head unit or assembly 36, which may be best seen in FIG. 3, and fed under the compaction roller 34. Focused heat energy is then applied to adhere the incoming material and the underlying previously laid material. With the combination of pressure and heat, the composite strips are consolidated into a previous applied layer to form an additional layer on the composite structure 12.

An example of an automated collation technique that may be used is described in U.S. Pat. No. 6,799,619 B2, entitled "Composite Material Collation Machine and Associated Method for High Rate Collation of Composite Materials." The contents of U.S. Pat. No. 6,799,619 B2 are incorporated herein by reference.

Referring now to the detection system 11, the light sources 13 are positioned to emit light arrays at the selected portion 18 of the composite structure 12. The light sources 13 are positioned at the acute angles 20 relative to the composite structure 12. In one embodiment of the present invention, the acute angles 20 are approximately greater than or equal to 2.degree. and are approximately less than or equal to 15.degree. Other angles may be used depending on the application. Any number of light sources may be utilized even though a specific number is shown.

The light sources 13 are positioned relative to the composite structure 12 via a mounting apparatus 40. The mounting apparatus 40 includes a main shaft 42, a secondary shaft 44, and a locking clamp 46 for adjusting the position of the light sources 13. The mounting apparatus 40, in turn, can be attached to the frame 48, to the detectors 14, to the bracket 50, or to some other object that defines a common position for both the light sources 13 and the detectors 14 to maintain a constant spatial relationship relative to one another.

Figure 4:
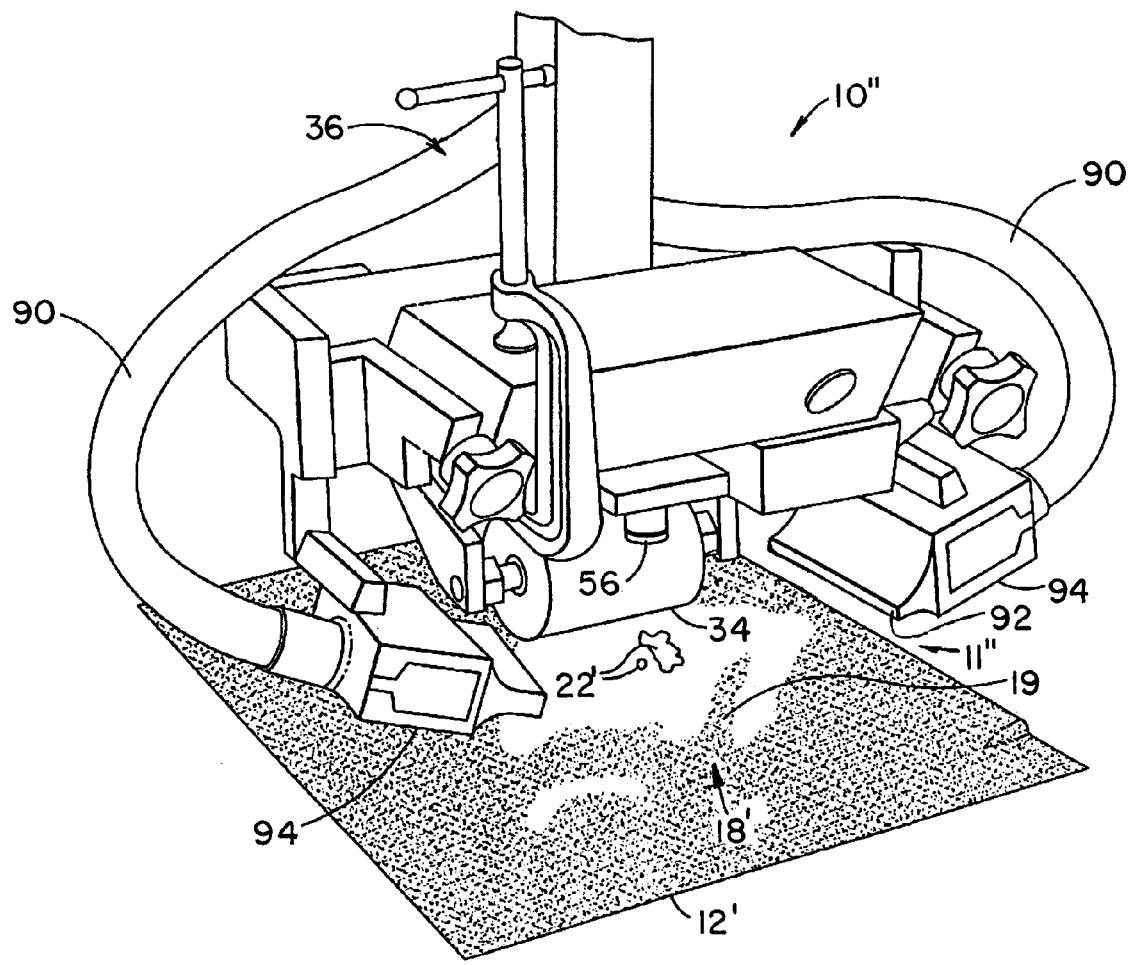
FIG. 4 is a perspective view of a fabrication system incorporating a flaw and FOD detection system in accordance with another embodiment of the present invention.

The light sources 13 may be selected from an infrared light or another type of light having an infrared component, such as a halogen light source or other incandescent light sources. In other embodiments, the light sources 13 are in the form of a fluorescent light source (e.g., white light LEDs, a low pressure/mercury filled phosphor glass tube, etc.), a strobe or stroboscopic light source, a noble gas arc lamp (e.g., xenon arc, etc.), a metal arc lamp (e.g., metal halide, etc.), or a laser (e.g., pulsed laser, solid state laser diode array, infrared diode laser array, etc.). The light from the light sources 13 may pass through optical fibers to the point of delivery, an example of which is shown in FIG. 4. The light sources 13 may include LEDs arranged in an array or cluster formation. In one specific embodiment, the light sources 13 include twenty-four LEDs mounted in an array upon a three-inch square printed circuit board.

In some embodiments, the light sources 13 are operated at a power level that increases the infrared (IR) component of the light arrays, which aids in the inspection of dark tow material, such as carbon. In this regard, exemplary power levels in the range of approximately one hundred fifty watts (150 W) and in the wavelength range of about seven hundred nanometers to one thousand nanometers (700 nm-1000 nm) may be used. However, the particular power levels and wavelengths for the light sources 13 depends at least in part on the speed and sensitivity of the detectors 14, the speed at which the material is being laid, the light delivery losses, and the reflectivity of the material being inspected.

The detectors 14 may be of various types and styles. A wide range of detectors may be used including commercially available cameras capable of acquiring black and white images. In one embodiment, the detectors 14 are in the form of a television or other type of video camera having an image sensor (not shown) and a lens 13 through which light passes when the cameras are in operation. Other types of cameras or image sensors can also be used, such as an infrared-sensitive camera, a visible light camera with infrared-pass filtration, a fiber optic camera, a coaxial camera, a charge coupled device (CCD), or a complementary metal oxide sensor (CMOS). The detectors 14 may be positioned proximate the composite structure 12 on a stand (not shown) or mounted to the frame 48 or a similar device. In embodiments of the present invention that do not include a reflective surface, the detectors 14 may be positioned approximately six inches from the top surface 52 of the composite structure 12, and mounted to the frame 48 by way of the bracket 50 and associated connectors 54. Also, any number of detectors may be utilized.

The controller 24 may be microprocessor based such as a computer having a central processing unit, memory (RAM and/or ROM), and associated input and output buses. The controller 24 may be a portion of a central main control unit, be divided into multiple controllers, or be a single stand-alone controller as shown.

The connectors 54 may be rivets, screws, or the like and used to mount the detectors 14 to the frame 48 in a stationary position. Alternatively, the connectors 54 may be a hinge-type connector that permits the light sources 13, the detectors 14, and associated assembly to be rotated away from the composite structure 12. This embodiment is advantageous in situations when there is a desire to access parts of the material placement device that are located behind the detectors 14 and associated assembly, such as during maintenance, cleaning, or the like.

The detection system 11 may also include filters 56 (only one is shown), which may be utilized in conjunction with the lens 58 for filtering the light passing therethrough. In one embodiment, the filters 56 are designed to filter the light such that the infrared component of or a certain infrared wavelength or range of wavelengths of the light is able to pass into the detectors 14. Thus, the filters 56 may prevent ambient visible light from entering the detectors 14 and altering the appearance of the captured image.

Other methods of filtering light can also be used to achieve the same, or at least used to provide a similar result. For example, the detectors 14 may be designed to include a built-in filter of equivalent optical characteristics. In addition, the filter 56 may be located between the lens 58 and the detectors 14. Alternatively, the detectors 14 may include image sensors that are sensitive in the infrared spectrum (i.e., an infrared-sensitive camera), thus eliminating the need for the filters 56.

The detection system 11 may also include a marking device 60 for marking the location of the defects and the FOD on the composite structure 12. The marking device 60 may be attached to the frame 48 and be triggered by the controller 24 or similar device when a flaw or FOD is detected. The marking device 60 may deposit ink, paint, or the like onto the composite structure 12 in areas where flaws and FOD have been detected. The markings on the composite structure 12 enable the location of the flaws and FOD to be subsequently and readily identified either automatically or manually. The marking device 60 may also be adapted to mark flaws with different colored ink than that used to mark FOD. Alternatively, other marking or indicating methods can also be used, such as markings utilizing a pump-fed felt-tip marker or a spring-loaded marking pen, indications via audio or visual alerts, and the like.

Figure 3:
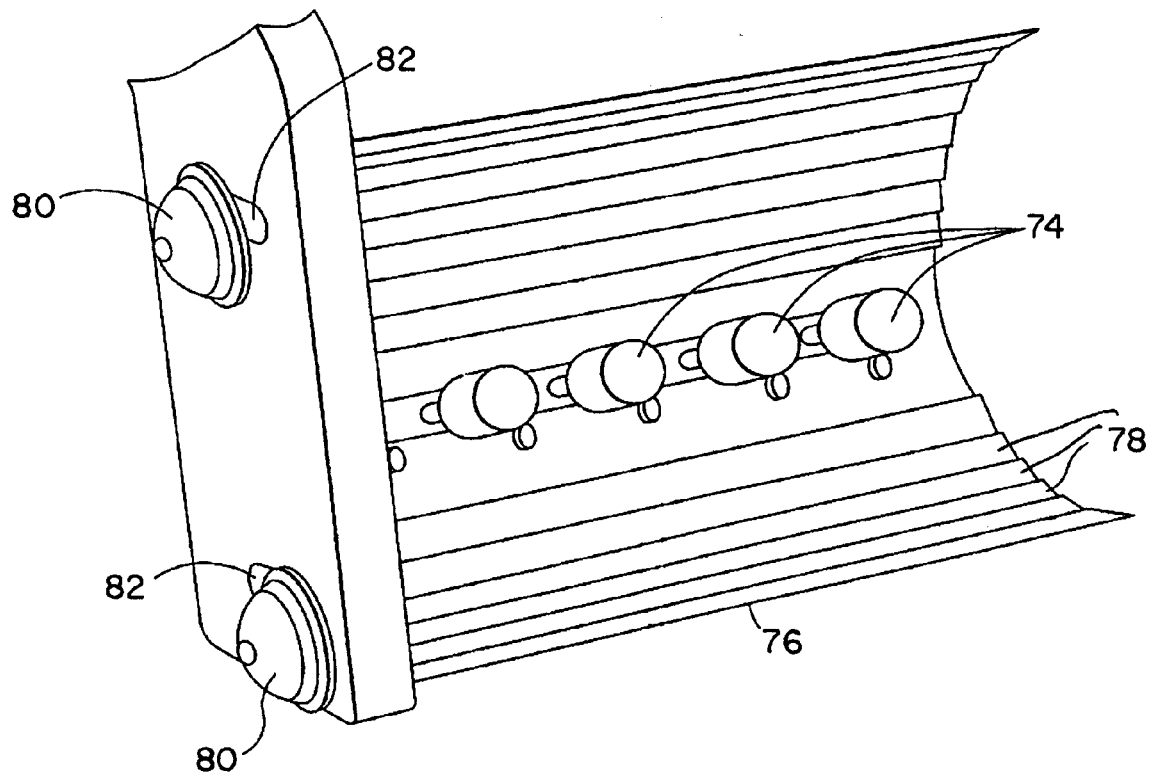
FIG. 3 is a perspective view of light sources according to the embodiment of FIG. 2.

Referring now to FIGS. 2 and 3, a perspective view of an application portion of a fabrication system 10' incorporating a flaw and FOD detection system 11' and a perspective view of light sources 13' are shown in accordance with another embodiment of the present invention. The detection system 11' includes two light sources 13' (only one is shown) positioned relative to the composite structure 12 and the compaction roller 34 on either side of a reflective surface 70 and a detector 14'. FIG. 2 illustrates an alternative embodiment of the hinge-type connector 54 that mounts the light sources 13', the detector 14', the reflective surface 70, and associated head assembly 36 to the frame 48 by way of the bracket 50.

The light sources 13 and 13' and the detectors 14 and 14', of FIGS. 1 and 2, may be translated or moved relative to a composite structure, such as the composite structure 12. The adjustability and moveability of the light sources 13 and 13' and detectors 14 and 14' provides flexibility in the capture of images of a composite structure. Sample systems including moveable cameras and light sources are described in detail in previously referred to U.S. patent application Ser. No. 10/217,805.

Although the light sources 13' are shown in the form of four halogen light bulbs 74, other quantities, types, and styles of illumination sources may be utilized. A light reflection element 76 is located near the light sources 13'. The reflection element 76 includes a series of light reflecting surfaces 78 that redirect the light towards the desired area to be illuminated. This levels the illumination across the top surface of a composite structure and eliminates, or at least substantially reduces, the areas of intense light (i.e., hotspots) created by the brightest portion of the light source. Hotspots can lead to errors during the processing of images. The light reflection elements 78 are particularly advantageous for illuminating the curved/contoured surfaces of the composite structures because the redirection of the light permits a larger portion of a composite structure to be evenly illuminated.

The reflection element 76 is curved around the light sources 13', such as in a parabolic shape. The reflection elements 78 are in the form of curved steps that are substantially parallel to the light source 13'. The distance between and the curvature of the reflection elements 78 may be selected for sufficient and even illumination generated from the sum of the two light sources 13'. This enables more consistent illumination of the composite structure 12, which prevents, or at least reduces, the image-processing errors due to inconsistent illumination of the composite structure 12. Alternatively, the shape and/or surface configuration of the reflection elements 78 may be modified using other techniques known in the art to produce consistent illumination and scattering of light.

In an exemplary embodiment, seventeen reflection elements are utilized and have an overall parabolic shape and a range of widths from about 0.125 inches at the outer edge of the reflection elements to about 0.250 inches at the center of the reflection elements. The reflection elements also have a uniform step height of about 0.116 inches. In other embodiments, however, the reflection elements 78 may be provided with different numbers of steps having different uniform or varying widths and different uniform or varying step heights.

Furthermore, the reflection elements 78 may be adjusted in order to direct the light produced by the light sources 13' and scattered by the reflection elements 78 toward the selected portion of a composite structure. For example, as shown in FIG. 3, the reflection elements 78 are mounted to the mounting apparatus 40 with fasteners 80. The fasteners 80, when loose, are capable of being slid within slots 82 to correspondingly adjust the angle of the reflection elements 78 relative to a composite structure. Once the reflection elements 78 are positioned appropriately, the fasteners 80 are tightened to secure the reflection elements 78 in the desired position. Adjustments of the reflection elements 78 can also be enabled by other methods, such as by electronic means that permit remote adjustment of the reflection elements 78.

The detectors 14 are positioned near the composite structure 12 and when in the form of cameras are positioned to capture images of the selected illuminated portion, which is typically immediately downstream of the nip point at which a composite tow is joined with the underlying structure.

The light sources 13, the detectors 14, the reflective surface 16, and any reflection elements 78, may be mounted on the head unit 23 to allow for continuous capture of real-time data of the composite structure 12. The real time data may be captured as the head unit 36 is transitioned across the composite structure 12 and as the composite strips are laid down or applied.

The bracket 50 may be fastened to the hinge type connector 54 via a suitable fastener, such as a thumbscrew or any other fastener that may be utilized and inserted through hole 72 and then tightened to secure the assembly in place for operation. The fastener may be loosened or removed, for example, to rotate the light source and detector assembly away from the compaction roller 34 and other parts of the fabrication system.

The reflective surface 70 may be positioned near the composite structure 12, and angled such that the reflective surface 70 reflects an image of the illuminated portion to the detectors 14. In one embodiment, the angle of the reflective surface 70 to the composite structure is about sixty-five degrees, but the reflective surface 16 can also be positioned at any appropriate angle in order to reflect images of the illuminated portion to the detectors 14. The detectors 14 may be positioned to point toward the reflective surface 70 in order to capture the close-range images of the illuminated portion from the reflective surface 70. More than one reflective surface 70 may also be utilized in further embodiments of the present invention in which the reflective surface 70 cooperate in order to direct the images of the illuminated portion to the detectors 14.

The reflective surface 70 may be in various positions relative to a selected portion, such as portion 18. Reflective surface 70 can also be utilized to allow the detectors 14 to be placed in an advantageous positions, which might otherwise be blocked by portions of the compaction roller 34 and/or other parts of the fabrication system.

The configuration illustrated in FIG. 2 aids in the capturing of images of curved/contoured surfaces of a composite structure since the reflective surface 70 is positioned close to the composite structure. In addition, this configuration permits the detectors 14 to be positioned away from a composite structure, to prevent interference between the detectors 14 and components of the fabrication system 11'. Further, the reflective surface 70 can also provide a "square on" view of the selected portion being inspected, which, in turn, can improve the ability to dimension the two gaps for pass/fail decisions.

Referring now to FIG. 4, a perspective view of a fabrication system 10" incorporating a flaw and FOD detection system 11" in accordance with another embodiment of the present invention is shown. The detection system 11" includes lights sources (not shown) that are at a remote location. The light sources generate light rays, which are passed through linear optical fiber arrays or fiber optic cable 90 to point of transmission 92 via light emitting heads 94. Light arrays are emitted from the fiber optic cable 90 toward the selected portion 18' of the composite structure 12' to detect flaws and FOD 22'. The use of fiber optic cables simplifies the number of components mounted on the head assembly.

Figure 6:
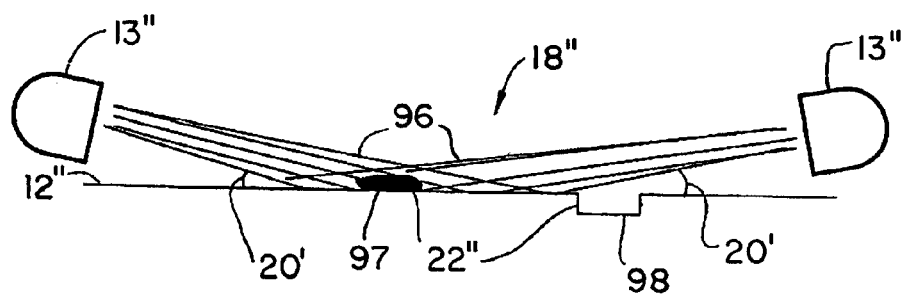
FIG. 6 is a side view illustrating low incident angle emission of light rays for the detection of flaws and FOD in a composite structure in accordance with an embodiment of the present invention.
Figure 5:
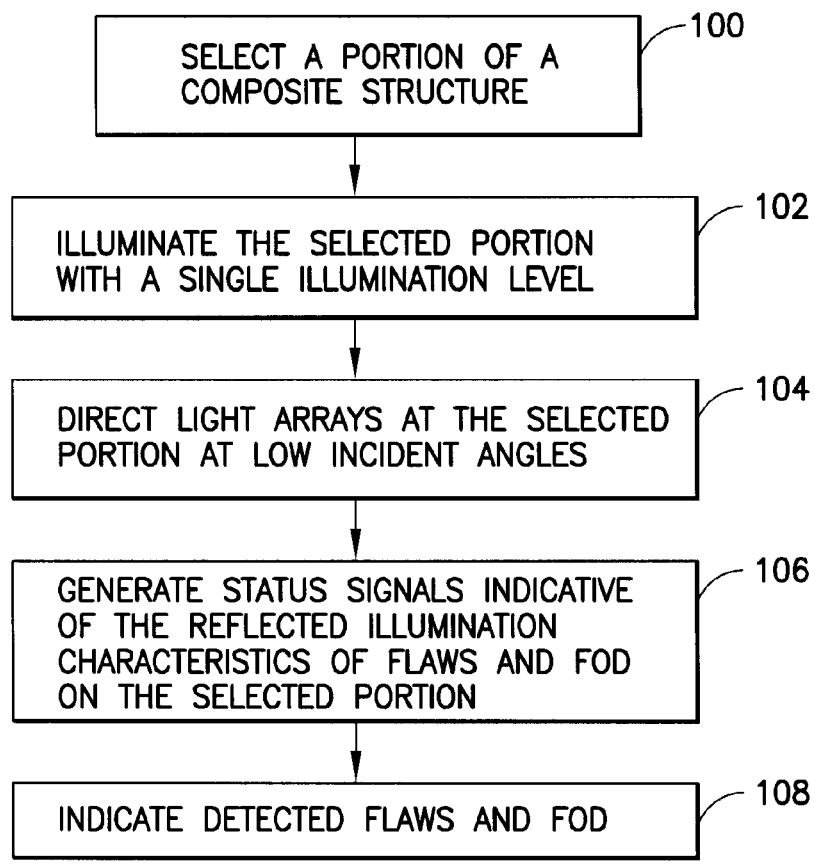
FIG. 5 is a logic flow diagram illustrating a method of detecting flaws and FOD in a composite structure in accordance with an embodiment of the present invention.

Referring now to FIGS. 5 and 6, a logic flow diagram illustrating a method of detecting flaws and FOD in a composite structure and a side view illustrating low incident angle emission of light rays for the detection of flaws and FOD in a composite structure are shown in accordance with an embodiment of the present invention.

In step 100, a portion 18" of concern of a composite structure 12" is selected. The portion 18" may include a segment or area of or may include the entire composite structure 12". In step 102, the light sources 13" are activated to illuminate the selected portion 18", which may include as stated selected areas of or the entire composite structure 12". The light rays 96, which may be in the form of arrays, are generated at a single illumination level. The illumination level is such that both flaws and FOD 22" may be detected simultaneously within the selected portion 18". The light source 13" may be activated throughout the material placement process.

In step 104, the light rays 96 are directed at the portion 18" and at low incident or acute angles 20' relative to the portion 18". Low incident lighting allows foreign objects to be easily distinguishable from a background of the laminate or the composite structure 12" on which material is being placed. As the composite structure 12" is illuminated, light is directed toward the edges of any FOD, such as FOD 97. This illumination allows for the shape and size of the FOD to be detected and is referred to as "backfield illumination". The low incident illumination also creates a shadow within flaw areas, such as within a gap, such as gap 98. In one example embodiment, the angles of the light arrays relative to the composite structure 12" are approximately greater than or equal to 2.degree. and less than or equal to 15.degree. The angles of the light arrays may be adjusted depending upon the conditions to provide desired image quality.

In step 106, detectors, such as detectors 14 and 14', monitor the portion 18" and generate status signals in response to the reflection of the light rays 96 off of the portion 18". The status signals contain information regarding the existence of flaws and FOD in the portion 18". The detectors 14 and 14' detect light reflection characteristics of the FOD. The contrast between the shadow and the composite structure is detected and thus allows for the detection of flaws or FOD. The flaw and the FOD 22" are thus detected simultaneously for the same illumination portion, in this example, portion 18". This allows for smaller areas of a structure to be examined at any single time. The detectors may detect flaws and FOD during the fabrication of the composite structure 12".

Figure 7:
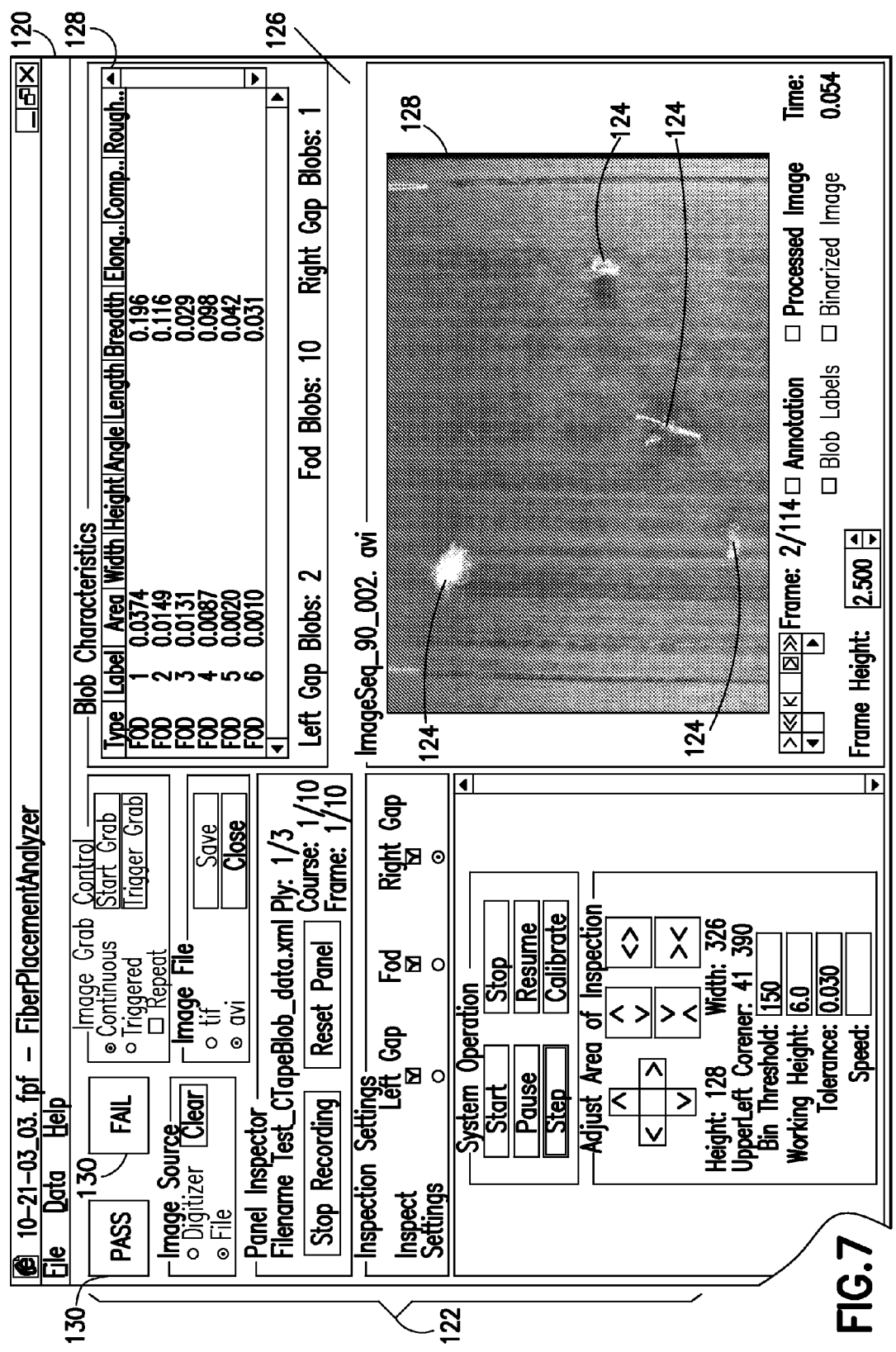
FIG. 7 is a front view of a display and user controls illustrating the detection of flaws and FOD in accordance with an embodiment of the present invention.

In step 108, the detected flaws and FOD 22" are indicated to a user via a display, such as that shown with respect to FIG. 7.

Referring now to FIG. 7, a front view of a user display screen 120 and user controls 122 illustrating the detection of flaws and FOD 124 in accordance with an embodiment of the present invention is shown. Although the operation and use of the display 120 is primarily described with respect to the embodiment of FIG. 1, it may be easily modified for and applied to other embodiments of the present invention. The user interface 28 includes the display 120, such as that on a computer monitor, and can also include an input device, such as a keyboard and mouse (not shown), for permitting an operator to move a cursor about the display 120 and input various system settings and parameters. The display 120 may be touch-sensitive for permitting the operator to input the desired settings by manually touching regions of the display screen.

The interface 28 includes a window 126 in which an image 128, of the composite structure 12, is displayed for viewing by an operator or other user. The image 128 may be in the form of an unprocessed or processed camera image. When processed the image 128 or a portion thereof may be binarized. During binarization, all shades of gray above a predetermined threshold value may be changed to white, while all gray shades below the threshold value may be changed to black to heighten the contrast of defects and improve the accuracy of defect detection. As an alternative or in addition to binarization, rates of light level change in the raw image and color changes in the images may be used to identify the defects and FOD.

The controls 122 allow for various user inputs to the system. The controls 122 may be used to adjust the binarization threshold. Generally, the setting of the binarization threshold involves a tradeoff between the sensitivity with which defects are detected and the resolution with which the defects are depicted. In one embodiment, the binarization threshold is set to about 128, which corresponds to the mid-point on the 8-bit digitizing range of 0 to 255. However, other binarization threshold values may be employed depending at least in part on the particular application, available lighting, camera settings, and other factors known in the art.

The controls 122 also allow the user to adjust or shift the viewing area within the window 126. During operation, the window 126 displays real-time moving video images of the illuminated portion of the composite structure 12 as the detectors 14 and/or the reflective surface 18 are moved relative to the composite structure 12. The controls 122 may be such to allow the user to input the maximum allowable dimensional parameters, the acceptable tolerances, as well as other known parameters for the flaws and FOD.

In addition to displaying images of the composite structure 12, the display screen 80 may also include a defect table 128, which lists the discovered flaws and FOD and provides related information thereof, such as location, size, and the like. The display 120 can further include status indicators 130 that notify the user whether a particular image area is acceptable or not acceptable based on predefined criteria, such as the maximum allowable dimensional parameters and tolerances.

Figure 8:
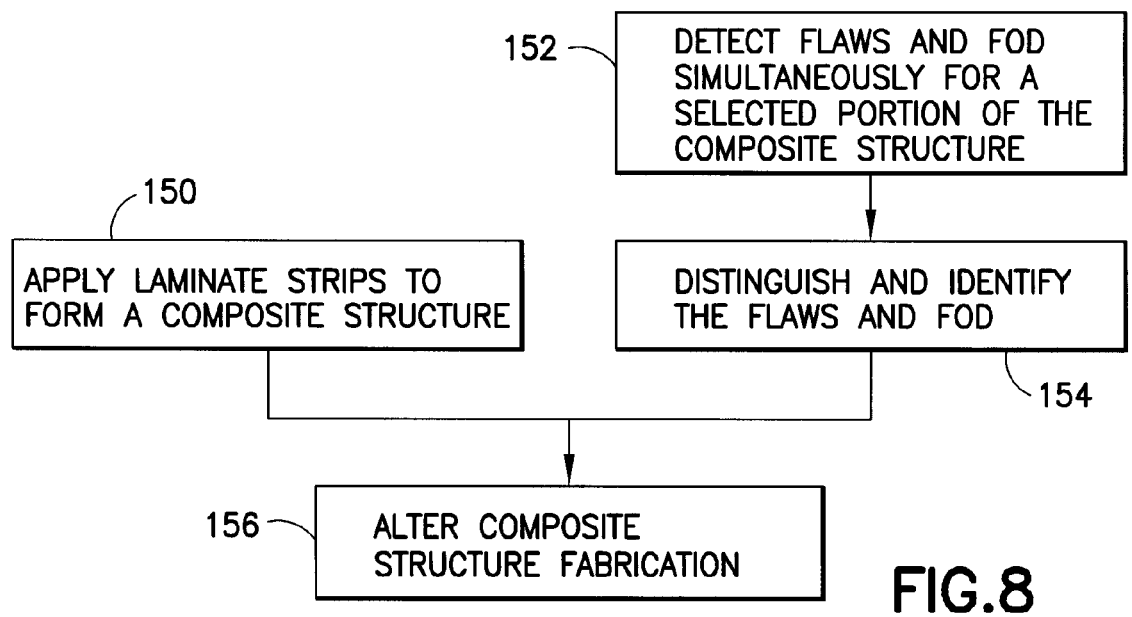
FIG. 8 is a logic flow diagram illustrating a method of fabricating a composite structure in accordance with an embodiment of the present invention.

Referring now to FIG. 8, a logic flow diagram illustrating a method of fabricating a composite structure in accordance with an embodiment of the present invention is shown. Although the logic flow diagram of FIG. 8 is primarily described with respect to the embodiment of FIG. 1, it may be easily modified to apply to other embodiments of the present invention.

In step 150, the fabrication system 10 applies the strips to form the layers 29 on the substrate 32 to form the composite structure 12. In step 152, the detection system illuminates selected portions of the composite structure 12 during the application of the strips to detect the flaws and FOD 22 as described above with respect to the method of FIG. 5.

In step 154, the detection system 11 distinguishes and identifies the flaws and FOD 22 and the location thereof and generates a composite structure defect signal. Examples regarding systems and methods for identifying defects in a composite structure during fabrication thereof are included in U.S. patent application Ser. No. 09/819,922, filed on Mar. 28, 2001, entitled "System and Method for Identifying Defects in a Composite Structure" and in U.S. patent application Ser. No. 10/217,805, filed on Aug. 13, 2002, entitled "System for Identifying Defects in a Composite Structure". The contents of U.S. patent application Ser. Nos. 09/819,922 and 10/217, 805 are incorporated herein by reference as if fully set forth herein.

In step 156, the fabrication system 10 may in response to the composite structure defect signal alter the operation thereof. The fabrication system 10 may cease further application of the strips until one or more portions of the composite structure 12 are repaired, may alter the manner in which the strips are applied, may adjust parameters of the fabrication system 10 or detection system 11, or may perform other tasks known in the art.

At any time upon or after the generation of the status signals and/or the defect signals the controller 24 may store data or images in the storage device 26 for future analysis and/or processing.

The above-described steps in the methods of FIGS. 5 and 8, are meant to be illustrative examples, the steps may be performed synchronously, continuously, or in a different order depending upon the application.

The present invention provides systems and methods for the simultaneous detection of flaws and FOD using a single illumination level. The present invention simplifies the detection of the flaws and FOD and allows for efficient identification and repair thereof.

While the invention has been described in connection with one or more embodiments, it is to be understood that the specific mechanisms and techniques which have been described are merely illustrative of the principles of the invention, numerous modifications may be made to the methods and apparatus described without departing from the spirit and scope of the invention as defined by the appended claims.

We claim:

1. A method of detecting flaws or FOD in a composite structure during the fabrication process of that structure comprising:

illuminating a portion of the composite structure across its entire width with a light source mounted to be in proximity with said composite structure and directing light rays at an acute angle relative to said portion of said composite structure of approximately greater than or equal to 2° and approximately less than or equal to 15°, said light source being positioned to emit light that illuminates a portion of the composite structure with bright field illumination and simultaneously illuminates another portion of the composite structure with dark field illumination;

monitoring said portion;

detecting flaws or FOD in said portion during fabrication of the structure in response to reflection of said light rays off of said portion by detecting the contrast between a shadow and the composite structure which allows for the detection of flaws and FOD simultaneously in said portion; and indicating said flaws or FOD in said portion to a user via a display.

2. A method as in claim 1 wherein said lights rays are generated at a single illumination level.

3. A method as in claim 1 wherein detecting said flaws or said FOD comprises detecting light reflection characteristics of said flaws and said FOD for the same illumination portion.

4. A method as in claim 1 wherein detecting said flaws or said FOD comprises detecting at least one flaw and said FOD simultaneously.

5. A method as in claim 1 wherein detecting said flaws or said FOD comprises detecting at least one flaw and FOD simultaneously for the same illumination portion.

6. A method as in claim 1, wherein said detecting said FOD comprises detecting contrast differences between said FOD and said portion.

7. A method as in claim 1 further comprising the step of generating status signals indicative of said FOD in said portion.

8. A method as in claim 7 further comprising the step of storing said status signals for future analysis or processing.

9. A method as in claim 1 further comprising the step of indicating said FOD in said portion to a user via a display.

10. A method of detecting flaws or FOD in a composite structure during fabrication of that structure comprising:

illuminating a portion of the composite structure across its entire width with a light source mounted to be in proximity with said composite structure and directing light rays at an acute angle relative to said portion of said composite structure of approximately greater than or equal to 2° and approximately less than or equal to 15°, said light source being positioned to emit light that illuminates a portion of the composite structure with bright field illumination and simultaneously illuminates another portion of the composite structure with dark field illumination, monitoring said portion;

detecting flaws or FOD in said portion during fabrication of the structure in response to reflection of said light rays off of said portion by detecting the contrast between a shadow and the composite structure which allows for the detection of flaws and FOD simultaneously in said portion;

generating status signals indicative of said flaws or FOD in said portion;

storing said status signals for future analysis or processing; and indicating said flaws or FOD in said portion to a user via a display.

11. A method as in claim 10 wherein generating said light rays comprises generating said lights rays at a single illumination level.

12. A method as in claim 10 wherein detecting said flaws or FOD comprises detecting light reflection characteristics of said flaws or FOD for the same illumination portion.

13. A method as in claim 10 wherein detecting said flaws or FOD comprises detecting said flaw and said FOD simultaneously.

14. A method as in claim 10 wherein detecting said flaws or FODS comprises detecting said flaws and said FOD simultaneously in response to illumination of said portion at a single illumination level.

15. A method as in claim 10, wherein said detecting said flaws or FOD comprises detecting contrast differences between said flaws or FOD and said portion.

16. A method of simultaneously detecting flaws or FOD in a composite structure during a fabrication process using a single illumination level comprising:

illuminating a portion of the composite structure across its entire width with a light source mounted to be in proximity with said composite structure and to illuminate said portion of said structure;

generating light rays and directing said light rays at an active angle relative to said portion of said composite structure of approximately greater than or equal to 2° and approximately less than or equal to 15°, said light source being positioned to emit light tat illuminates a portion of the composite structure with bright field illumination and simultaneously illuminates another portion of the composite structure with dark field illumination;

detecting flaws and FOD simultaneously in said portion in response to reflection of said light rays of said portion by detecting the contrast between a shadow and the composite structure which allows for the detection of flaws and FOD simultaneously in said portion; and indicating said flaws or FOD in said portion to a user via a display.

* * * * *